United States Patent
Mickley et al.

(10) Patent No.: US 7,470,252 B2
(45) Date of Patent: Dec. 30, 2008

(54) EXPANDABLE MULTI-PORT THERAPEUTIC DELIVERY SYSTEM

(75) Inventors: Timothy J. Mickley, Elk River, MN (US); Maria Palasis, Wellesley, MA (US); Toby Freyman, Waltham, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 51 days.

(21) Appl. No.: 10/942,046

(22) Filed: Sep. 16, 2004

(65) Prior Publication Data
US 2006/0058815 A1 Mar. 16, 2006

(51) Int. Cl.
*A61M 29/00* (2006.01)
*A61M 31/00* (2006.01)
*A61M 37/00* (2006.01)

(52) U.S. Cl. .............. 604/103.02; 604/96.01; 604/106

(58) Field of Classification Search .......... 604/20, 604/96.01, 99.04, 103, 102.02, 103.01, 103.02, 604/103.05, 105, 106, 107, 532, 266, 93.01; 600/37
See application file for complete search history.

(56) References Cited

U.S. PATENT DOCUMENTS

| | | | |
|---|---|---|---|
| 5,681,281 A | | 10/1997 | Vigil et al. |
| 5,713,853 A | | 2/1998 | Clark et al. |
| 5,713,863 A | * | 2/1998 | Vigil et al. .................. 604/104 |
| 6,033,397 A | * | 3/2000 | Laufer et al. .................. 606/27 |
| 6,045,565 A | | 4/2000 | Ellis et al. |
| 6,197,013 B1 | | 3/2001 | Reed et al. |
| 6,203,559 B1 | * | 3/2001 | Davis et al. .................. 606/198 |
| 6,210,392 B1 | | 4/2001 | Vigil et al. |
| 6,248,112 B1 | | 6/2001 | Gambale et al. |
| 6,263,236 B1 | * | 7/2001 | Kasinkas et al. .............. 604/21 |
| 6,280,413 B1 | * | 8/2001 | Clark et al. .................. 604/104 |
| 6,280,414 B1 | * | 8/2001 | Shah et al. .................. 604/104 |
| 6,306,163 B1 | * | 10/2001 | Fitz .......................... 623/1.12 |
| 6,537,247 B2 | * | 3/2003 | Shannon ................ 604/103.05 |
| 6,559,267 B2 | * | 5/2003 | Kaufhold et al. ............. 528/76 |
| 6,616,650 B1 | * | 9/2003 | Rowe ........................ 604/509 |
| 6,656,155 B2 | * | 12/2003 | Freyman ................ 604/103.01 |
| 6,955,661 B1 | * | 10/2005 | Herweck et al. ............. 604/264 |
| 2002/0082469 A1 | * | 6/2002 | Taheri ........................ 600/37 |
| 2004/0044308 A1 | | 3/2004 | Naimark et al. |
| 2004/0064093 A1 | * | 4/2004 | Hektner et al. ......... 604/103.01 |
| 2004/0153048 A1 | | 8/2004 | Vigil et al. |

FOREIGN PATENT DOCUMENTS

| EP | 0 664 104 A2 | 1/1995 |
|---|---|---|
| WO | WO 93/13826 | 7/1993 |

* cited by examiner

*Primary Examiner*—Nicholas D Lucchesi
*Assistant Examiner*—Christopher D Koharski
(74) *Attorney, Agent, or Firm*—Kenyon & Kenyon LLP

(57) ABSTRACT

The present invention provides a systems that delivers therapeutic to the inner lumens, chambers, cavities, and vessels of the body. A therapeutic delivery device for delivery of therapeutic to a target site within the body of a patient is provided. This device may include a catheter, an expandable multi-port housing fluidly coupled to the catheter and a sheath. The multi-port housing in this device may be sized to travel within a lumen of a patient and may be adapted to expand from a first configuration to a second configuration. The multi-port housing may also contain at least two ejection ports coupled to an internal lumen of the multi-port housing.

12 Claims, 10 Drawing Sheets

EXPANDABLE MULTI-PORT THERAPEUTIC DELIVERY SYSTEM

FIELD OF THE INVENTION

The present invention regards the delivery of therapeutic to a target site in the body of a patient. More specifically, the present invention regards systems, devices, and methods that employ an expandable multi-port therapeutic delivery device to deliver therapeutic to a target vessel or other target site in the body of a patient.

BACKGROUND

The delivery of therapeutic to a target site in the body of a patient is an often repeated procedure of contemporary medicine. Delivery procedures can range from minimally invasive techniques such as hypodermic needle delivery and intra-luminal catheter delivery of therapeutics, to more invasive delivery techniques such as the direct manual injection of therapeutic into the myocardium of the heart during open heart surgery.

Intra-luminal therapeutic delivery procedures include guiding an injection catheter within a lumen of the body to a target site, delivering therapeutic from the catheter to the target site, and withdrawing the catheter from the target site. When the target area is large, such as an entire chamber of the heart, a medical practitioner may need to repeat the delivery portion of the procedure many times in order to adequately dispense the therapeutic over the entire target area. As the number of injection points increases, the time necessary to complete the procedure increases and the uniformity of the spacing and depth of each injection may vary, this despite the best efforts of the medical practitioner.

SUMMARY OF THE INVENTION

The present invention provides methods, systems, and devices that deliver therapeutic to the inner lumens and vessels of the body. In one embodiment, a therapeutic delivery device for delivery of therapeutic to a target site within the body of a patient is provided. This device may include a catheter, an expandable multi-port housing fluidly coupled to the catheter and a sheath. The multi-port housing in this device may be sized to travel within a lumen of a patient and may be adapted to expand from a first configuration to a second configuration. The multi-port housing may also contain at least two ejection ports coupled to an internal lumen of the multi-port housing. In some embodiments the multi-port housing is a bladder, while in others it is a frame or a group of outwardly extending arms. In each case, the device is configured to deliver therapeutic to a remote site in the body of a patient.

DETAILED DESCRIPTION

Figure 1:
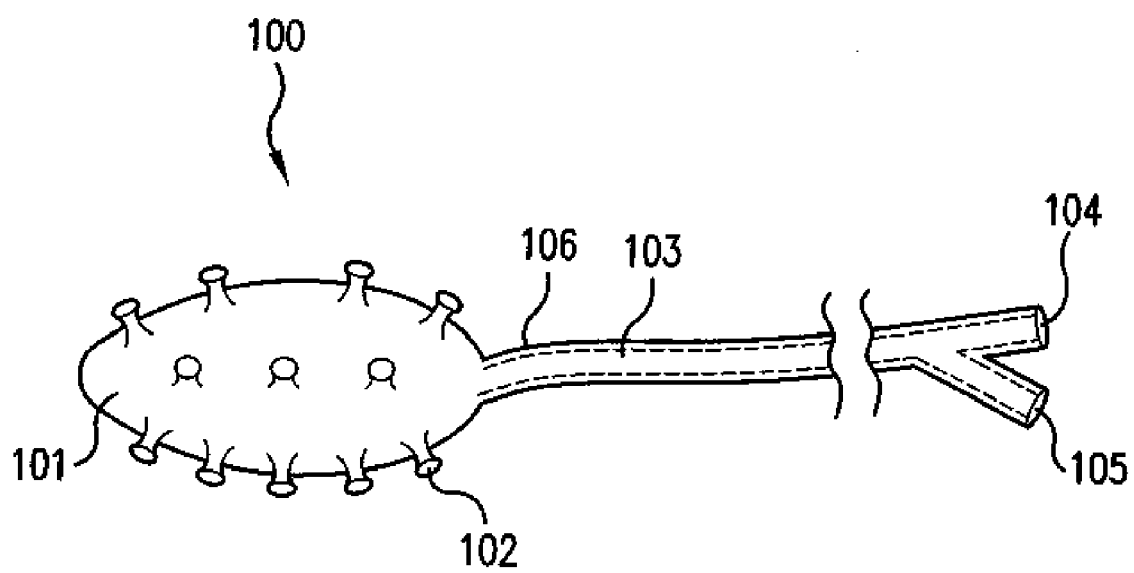
FIG. 1 is a side view of an embodiment of the present invention.

FIG. 1 is a side view of an expandable multi-port therapeutic delivery device 100 in accord with the present invention. The expandable multi-port delivery device 100 in FIG. 1 contains ports 102, multi-port housing 101, catheter 106, lumen 103, inflation port 104, and therapeutic supply port 105. In this embodiment, as well as in others, the catheter 106 may be constructed of the same material as that comprising the multi-port housing 101. Alternatively, the catheter may be constructed of one material, e.g., nylon, while the multi-port housing 101 may be constructed of or reinforced with another, e.g., nitinol. Likewise, the ports may be constructed of or reinforced with one material, e.g., nitinol, while the housing may be constructed of another, e.g., rubber. As can be seen, the catheter 106 may contain an inflation port 104 and be coupled to a therapeutic supply at port 105. During a medical procedure, the catheter 106 may be used to control the positioning of the multiple-port housing 101, to inflate and contract the multi-port housing 101, and to deliver therapeutic to and out of the injection ports 102 of the multi-port housing 101. While the multi-port housing 101 is depicted as a balloon in this example, it may take on numerous other configurations. For example, it may be the frame shown in later embodiments.

As can be seen, the ports 102 of the multi-port housing may be raised above the surface of the multi-port housing and may contain internal lumens that allow for the passage of therapeutic therethrough. When the ports 102 are raised or otherwise extend from the housing they will be better able to pierce into tissue when the housing 101 is expanded. For instance, when the housing 101 is expanded, the ports 102 may become seated in the tissue due to their position.

While a single lumen 103 is shown in the device 100, multiple lumens may be present in the device 100 as well. Separate lumens may be used to control the inflation of the housing 101 and the delivery of therapeutic. They may be used for other functions as well. The ports 102 may be positioned on the multi-port housing 101 in aligned rows and columns as well as other patterns. The ports 102 may also be randomly positioned on the multi-port housing 101. The ports 102 may even be placed in a single area or region of the housing 101 such that only a portion of the myocardium or other target area may receive therapeutic. The ports 102 may also be aligned along a surface arc of the housing 101.

The flow of fluid or therapeutic through the ports 102 may be regulated by some sort of valve or other mechanism. In each case, it is preferred that the therapeutic be delivered to each of the ports 102 in uniform quantities, although other configurations, where only certain ports receive therapeutic, where the ports 102 have different shapes and sizes, and where the rate of flow through the ports 102 varies, are all also within the spirit and scope of the present invention.

Figure 2:
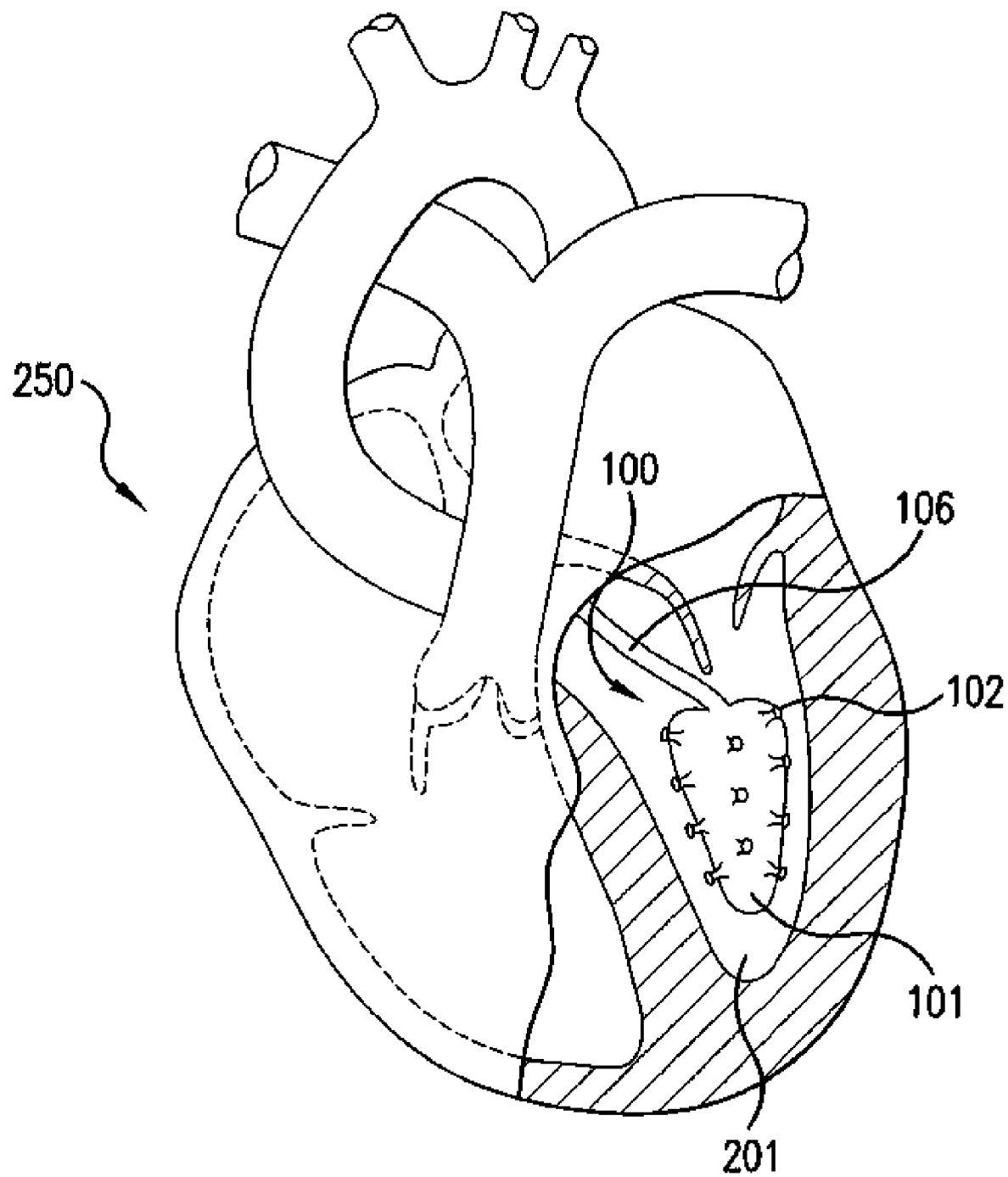
FIG. 2 is a side view of the device of FIG. 1 as it may be employed in the left ventricle of the heart of a patient.

FIG. 2 shows the delivery device 100 of FIG. 1 as it may be used to delivery therapeutic to the left ventricle 201 of a beating heart 250. As can be seen, the multi-port housing 101 is sized and dimensioned such that it may be snaked to and positioned within the left ventricle. While the multi-port housing 101 is shown being snaked through the aortic valve it may also be snaked through other valves of the heart to reach this and other target areas. As can also be seen, when the multi-port housing 101 is inserted into the left ventricle it may be sized such that it does not touch any of the internal walls of the chamber when the housing 101 is deflated. By comparison, when it is inflated, the multi-port housing 101 may be shaped to closely conform to the internal dimensions of the left ventricle or other target area. By having the multi-port housing 101 closely mimic the dimensions of the target vessel, therapeutic delivered via the ports 102 is more apt to be evenly delivered throughout the target area.

Therapeutic may be delivered before, during, and after the multi-port housing 101 is expanded. In other words, therapeutic may be dispensed to the surrounding fluid upon reaching the target area, to the tissue after the housing 101 is expanded, and then to the surrounding fluid again after the housing 101 is deflated and prior to its removal from the target area. Therapeutic may also be delivered during only portions of this cycle, as may be required by the medical procedure being performed.

In this embodiment, the multi-port housing 101 may be an expandable bladder coupled to a catheter 106 with an internal lumen. The housing may comprise a highly compliant material so that it will readily conform to the shape of the vessel it may reside within. The housing 101 may be made with resilient and/or flexible material including, but not limited to, latex, silicone, polyurethane, rubber, nylon, and/or shape memory polymers. The ports 102 may take on various shapes and configurations. In FIG. 1 the ports 102 have a frustum like configuration while they may also be funnel shaped and obconic, as well as many other shapes. In a preferred embodiment, the ports 102 are in fluid communication with the lumen 103 within the catheter 106 and have piercing edges capable of piercing the target tissue.

In use, once the housing 101 is positioned at a target site, compressed gas or a liquid such as saline may be piped into the device through the inflation port to inflate the housing 101. Then, after the inflation port is closed, therapeutic may be forced from the therapeutic supply port 105, through the lumen 103, and out the ports 102. The therapeutic may be forced, manually or automatically, from a storage vessel. In so doing, therapeutic may be delivered to numerous points without the need to reposition the delivery device 100 within the target vessel. When the desired amount of therapeutic has been delivered to the target site, the delivery end may be deflated so that the ports will no longer be penetrating into the myocardium. The housing 101 may be then repositioned and the inflation and therapeutic cycle repeated.

Figure 3:
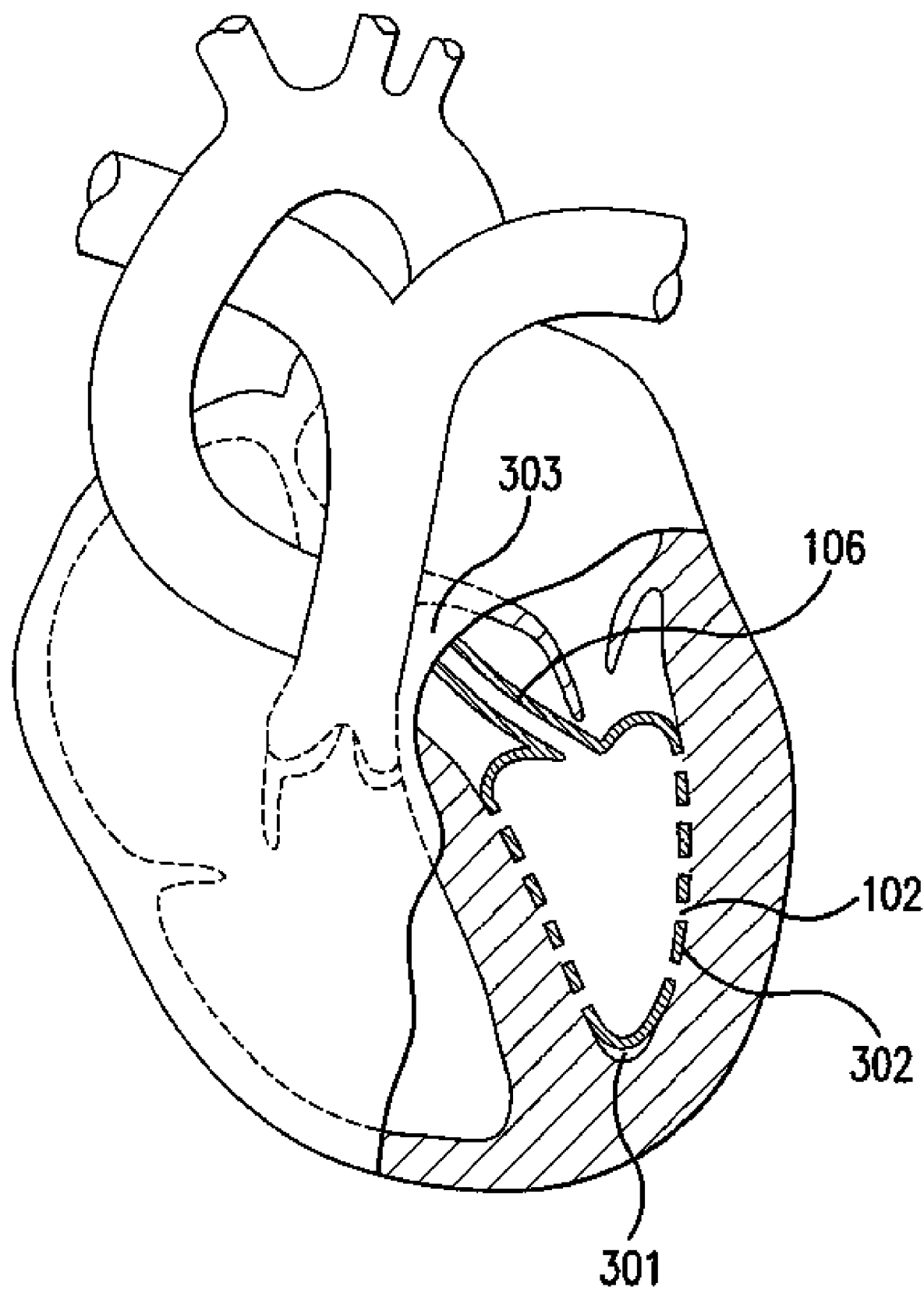
FIG. 3 is a side view of the device in FIG. 1 as it may be employed in the left ventricle of the heart of a patient.

FIG. 3, shows the multiple-port housing 101 of the previous two illustrations in an expanded state. In FIG. 3, the ports 102 are positioned against and have penetrated into the walls of the heart chamber. There is no space 302 around most of the chamber and only a small space 301 near the bottom. In other configurations, the multi-port housing 101 may be sized to leave no space whatsoever or to cover only a portion of the ventricle or other vessel wall.

As can also be seen in FIG. 3, the catheter 106 is sized to fill the opening in the aortic valve 303. Comparatively, in other embodiments, the catheter 106 may have a smaller diameter such that the mitral valve or other entry point to the heart may more readily allow fluid to pass when the procedure is being performed.

Therapeutic delivery may also be accomplished in this and the other embodiments by coating the surface of the multi-port housing 101 with therapeutic to be delivered. Additionally, the housing 101 may also be porous so as to allow the therapeutic to diffuse through the pores of the housing into the target site. The ports and micropores, which provide for this diffusion, may be sized in this and the other embodiments such that the therapeutic is able to pass through them only when positive pressure is exerted to urge the therapeutic through the ports or micro-pores.

Figure 4:
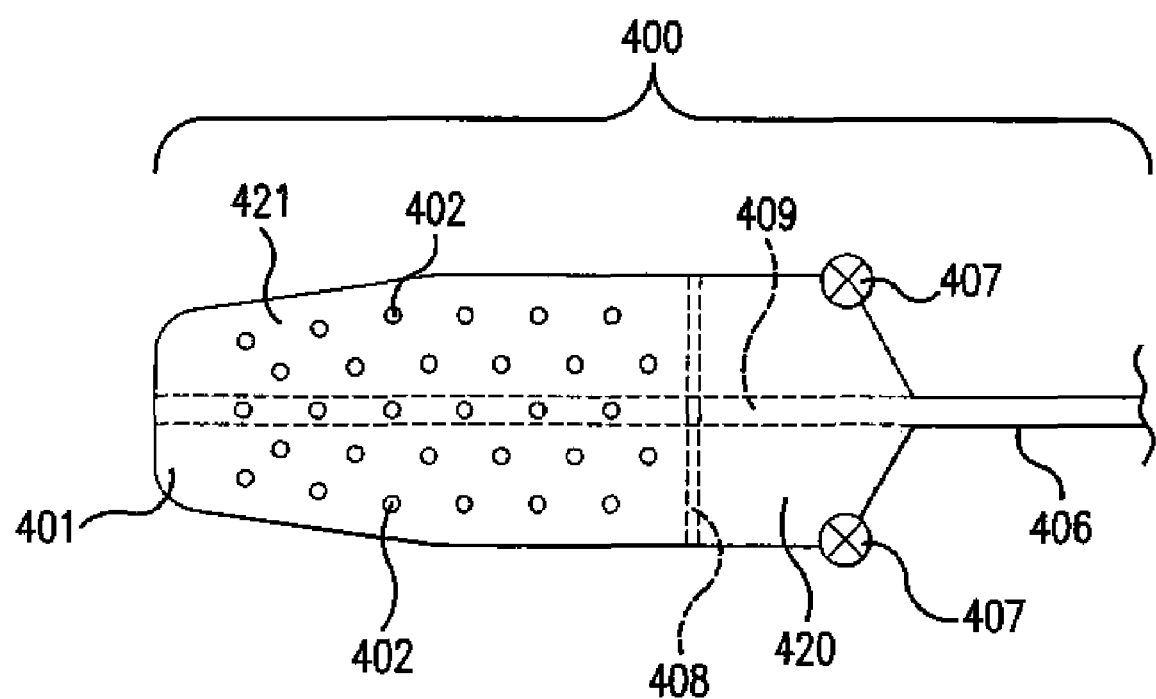
FIG. 4 is a side view of another embodiment of the present invention.

FIG. 4 shows an embodiment of the present invention similar to the device of FIGS. 1-3 except that the multi-port housing 401 is bifurcated into two chambers via a partition 408. The multi-port therapeutic delivery device 400 includes a first chamber 421, a second chamber 421, valves 407, a multi-port housing 401, ports 402, a catheter 406, a catheter lumen 409, and a partition 408. In this embodiment, the lumen 409 extends into the first chamber 421 past the partition 408. In so doing, the device of FIG. 4 allows blood or other fluids to flow between valves 407 when the Figure is inflated. Thus, therapeutic may be delivered through the lumen 409, housing 401, and the ports 402 of the first chamber while blood or some other fluid may continue to flow through the second chamber. While the shunt area or second chamber 420 is in the proximal section of this embodiment, which is preferred if the device is used in the left ventricle, the shunt area may also run along a longitudinal axis of the device, thereby allowing blood or some other fluid to pass through a lumen that is otherwise occluded by the expanded device. The shunt area may be in other positions as well.

Figure 5:
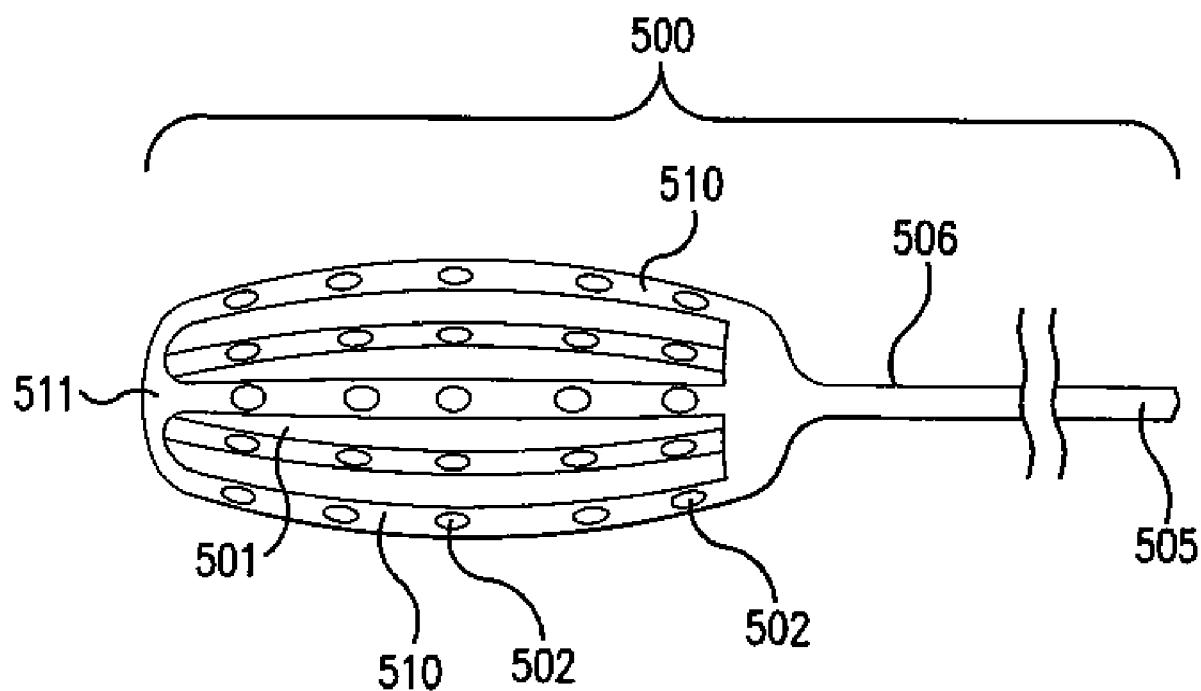
FIG. 5 is a side view of another embodiment of the present invention.

In the embodiment of FIG. 5, the multi-port housing 501 comprises a frame having two or more flexible struts 510. These struts 510 may have lumens within and may have one or more ports 502 fluidly coupled to those lumens. Alternatively, only some of the struts may contain ports and lumens. Moreover, the ports may be identically positioned on each strut in the delivery end as well as be uniquely positioned on each of the struts. This frame can take on many figurations and contain many or only a few struts 510. As can be seen, the struts 501 of the frame in the embodiment are aligned in an arcuate configuration where, when expanded, would define an obround structure. Comparatively, when the frame is unexpanded, as shown, the frame takes on a more elongate configuration.

Figure 6:
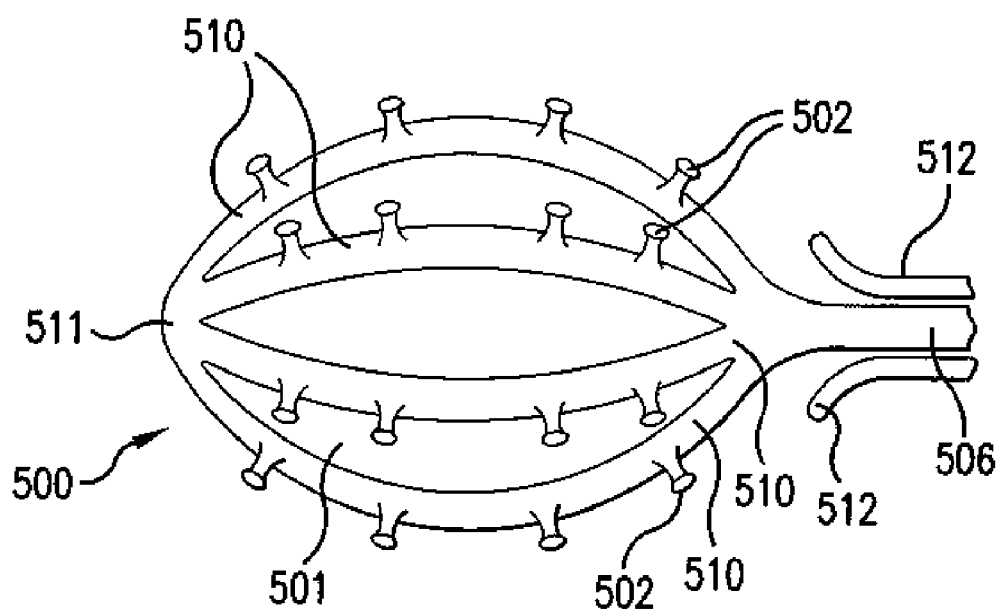
FIG. 6 is a side view of the device of FIG. 5 in an expanded and extended position.
Figure 7:
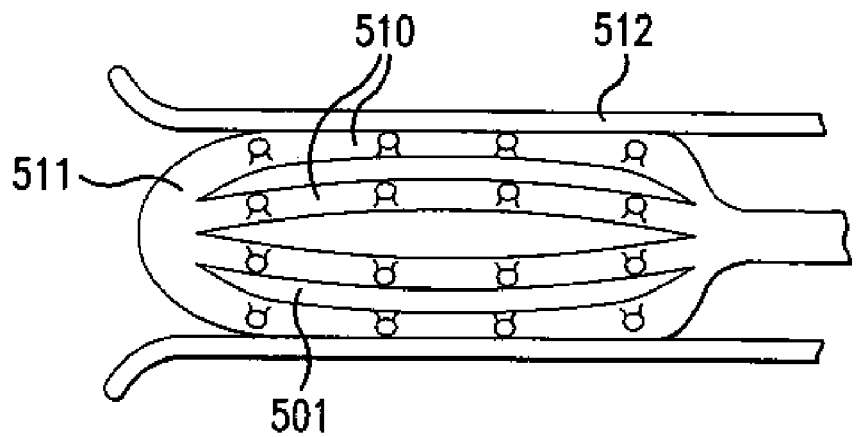
FIG. 7 is a side view of the device of FIG. 5 in a retracted position.

As can be seen, the housing 501 is coupled to a catheter 506, which is coupled to a therapeutic supply line 505. In FIG. 6, the catheter 506 is shown surrounded by a sheath or cover 512. When the housing is extended from the sheath 512, it may expand and when it is pulled back into the sheath it may contract. Alternatively, the frame or housing 501 may remain in a contracted orientation even after it is extended from the sheath 512 and may, instead, expand when therapeutic is dispensed into the lumens and out the ports 502. FIG. 7, shows the frame 501 retracted into the cover 512. This may be both before or after the device 500 has been used for a medical procedure.

The biasing of the frame into an open or closed configuration can be performed by pre-shaping the struts during fabrication. The struts 510 may be formed from nitinol or some other material having a shape retaining characteristic. Likewise, the tip 511 of the frame 501 may also be formed of a different material in order to force the frame open or closed, this may be in addition to a natural biasing of the struts or it may be the sole mechanism generating an opening force on the frame.

As described above, once in the expanded state, the ports 502 on the frame 501 may penetrate tissue at the target site and therapeutic may be delivered through the ports 502 to the target tissue. Once the appropriate amount of therapeutic is delivered, the frame 501 may be retracted from the target site, preferably within the target site, but it may be outside of it as well.

Figure 8:
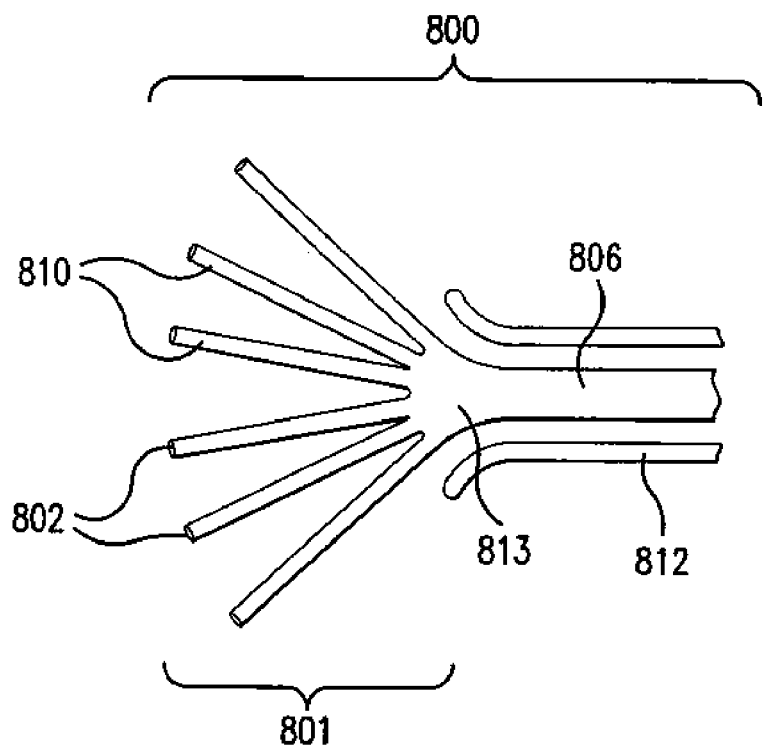
FIG. 8 is a side view of another embodiment of the present invention.

In FIG. 8, the injection device 800 the multi-port housing comprises a bundle of hollow flexible tubes or arms 810 that are fluidly connected to the catheter 806 through the junction 813. While six flexible tubes or arms 810 are shown, any number may be employed to accommodate the varying sizes of each target site. In use, the multi-port housing 801 would be urged from the sheath 812 and towards a target area. The orifices may be placed adjacent to or into target tissue and therapeutic may be dispensed therefrom. The tubes or struts 810 may be made from various materials. In a preferred embodiment, the struts 810 are rigid enough to penetrate the target tissue and embed the ports 802 therein.

Figure 9:
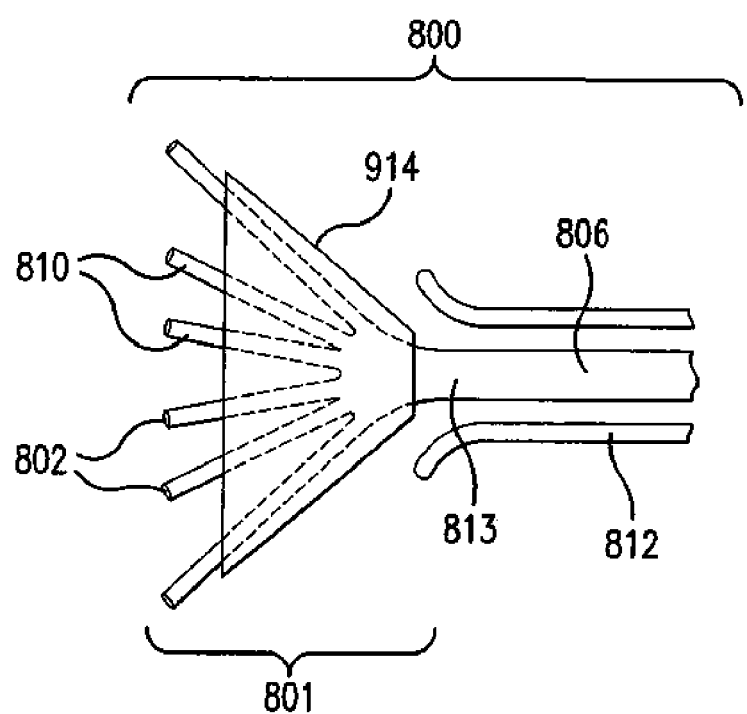
FIG. 9 is a side view of the device of FIG. 8 with a housing wrap.

FIG. 9 is another embodiment that operates similar to the embodiment in FIG. 8. As seen in FIG. 9, the housing wrap 914 partially covers at least a portion of the distal ends of tubes 810. The housing wrap 914 does not penetrate into the target site, and hence limits the distance the ports 802 of the tubes 810 may travel into the target site. The housing wrap may be attached to any of the tubes 810 or the catheter 806. The housing wrap 914, the struts 810, or both, may have a memory-shape or elastic characteristic tending to bias the tubes in one desired direction or configuration.

Figure 10:
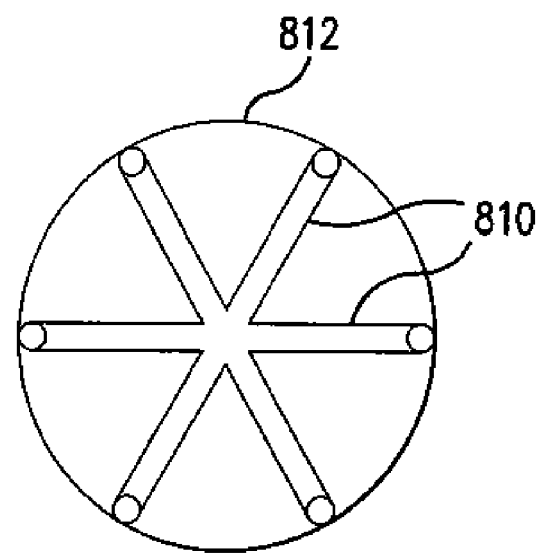
FIG. 10 is an end-view of the device in FIG. 11 taken along line 11-11.

FIG. 10 shows the injection device 800 with the tubes 810 withdrawn inside the first sheath 812 prior to the device 800 arriving at the target site. When the device 800 is placed at the target site, the housing 801 is urged out of the sheath 812 and towards the target site. The tubes 810 then penetrate the target site, wherein the agent may then be supplied through the catheter 806. Once the agent has been delivered, the device 800 is urged proximally, so that the tubes 810 are at least partially withdrawn into the sheath 812. A dye may be introduced into the lumen of the sheath 812 and forced out the distal end of the sheath 812. This may assist in observing the procedure being performed.

Figure 11:
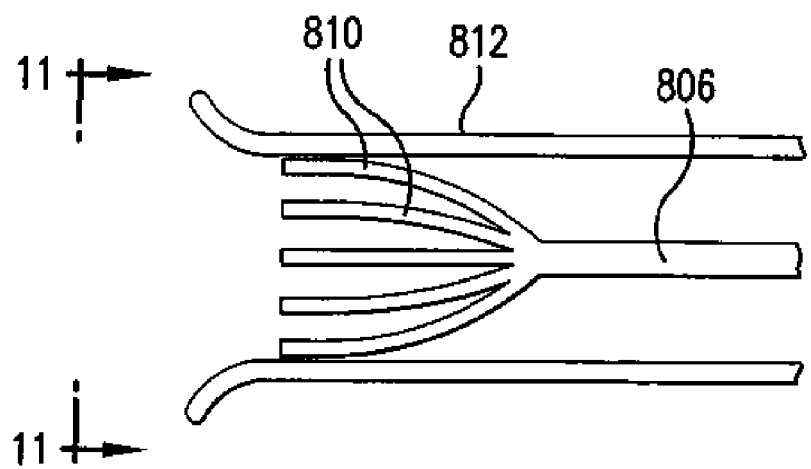
FIG. 11 is a side view of the device of FIG. 8 in a retracted position.

FIG. 10 shows the end view of the device in FIG. 11 along line 11-11. As can be seen, the sheath 812 is circular and the struts 810 are uniformly spaced within it. In other embodiment, the struts may not be evenly spaced, but may, rather, be randomly positioned as well as grouped in other patterned configurations.

Figure 12:
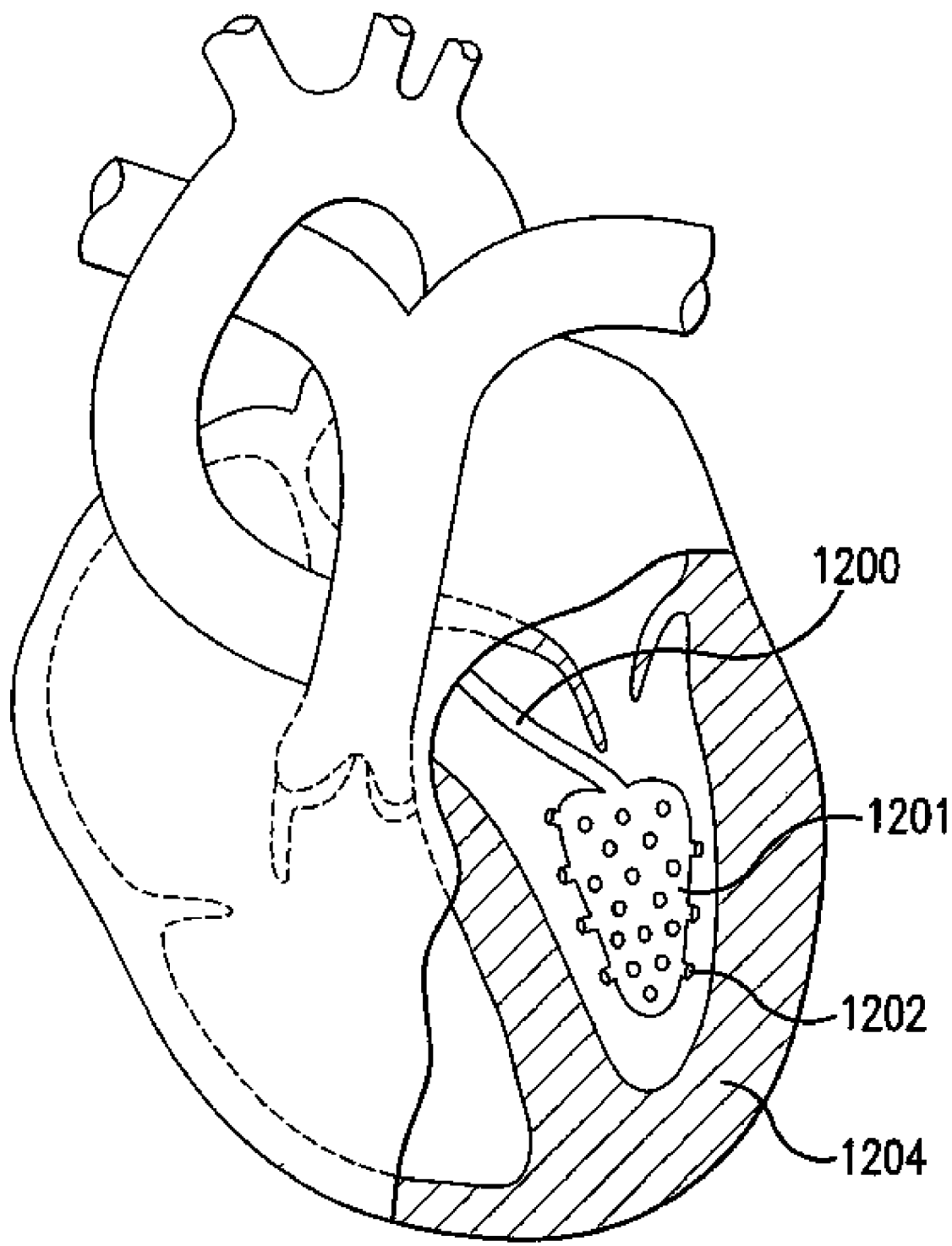
FIG. 12 is a side view of another embodiment of the present invention when the left ventricle is relaxed.
Figure 13:
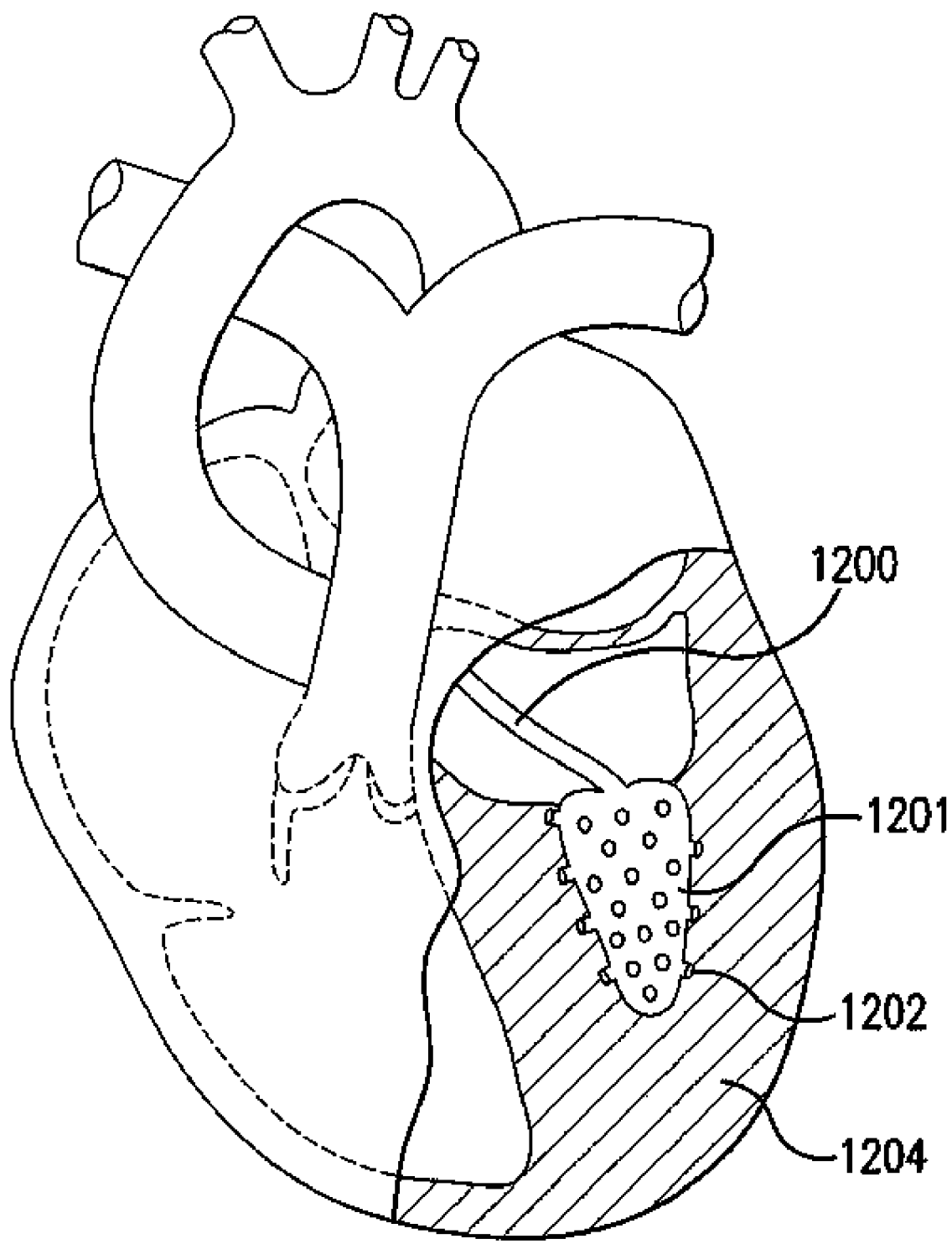
FIG. 13 is a side view of the embodiment from FIG. 12 when the left ventricle is contracted.

FIGS. 12 and 13 show a therapeutic delivery device in the left ventricle while the ventricle is relaxed (diastole) and pumping (systole). As can be seen the therapeutic delivery device 1200 in both figures has been sized to contact the ventricle wall 1204 when the ventricle is contracted. When the ventricle wall 1204 contacts the device 1200, the ports 1202 of the multi-port housing 1201 may penetrate into the wall. The housing, in this instance has been sized to urge the ports into the ventricle wall when the ventricle wall is pumping but not to contact the ventricle wall 1204 when the ventricle is in a relaxed state. As the contraction and relaxation cycle is repeated therapeutic may be cyclically pumped into the multi-port housing such that it may be injected into the ventricle wall 1204 when the ports 1202 are in contact with or penetrating into the wall 1204. The ports 1202 may contain ball valves that themselves further retard the expulsion of therapeutic until the ports are in contact with the myocardium.

In addition to being sized to simply fit within the ventricle or other vessel when the vessel is in a reduced or constricted position, the housing may also be sized to fit within or be larger than a vessel when it is in a relaxed or expanded state. For instance, the housing may be slightly larger than an artery when the housing is used in angioplasty procedures.

The term "therapeutic" as used herein includes pharmaceutically active compounds, nucleic acids with and without carrier vectors such as lipids, compacting agents (such as histones), virus (such as adenovirus, adenoassociated virus, retrovirus, lentivirus and a-virus), polymers, hyaluronic acid, proteins, cells and the like, with or without targeting sequences. The therapeutics administered in accordance with the invention include the therapeutic agent(s) and solutions thereof.

Specific examples of therapeutics used in conjunction with the present invention include, for example non-genetic therapeutic agents, a biomolecule, a small molecule, or cells.

Exemplary non-genetic therapeutic agents include anti-thrombogenic agents such heparin, heparin derivatives, prostaglandin (including micellar prostaglandin E1), urokinase, and PPack (dextrophenylalanine proline arginine chloromethylketone); anti-proliferative agents such as enoxaprin, angiopeptin, sirolimus (rapamycin), tacrolimus, everolimus, monoclonal antibodies capable of blocking smooth muscle cell proliferation, hirudin, and acetylsalicylic acid; anti-inflammatory agents such as dexamethasone, rosiglitazone, prednisolone, corticosterone, budesonide, estrogen, estradiol, sulfasalazine, acetylsalicylic acid, mycophenolic acid, and mesalamine; anti-neoplastic/anti-proliferative/anti-mitotic agents such as paclitaxel, epothilone, cladribine, 5-fluorouracil, methotrexate, doxorubicin, daunorubicin, cyclosporine, cisplatin, vinbiastine, vincristine, epothilones, endostatin, trapidil, halofuginone, and angiostatin; anti-cancer agents such as antisense inhibitors of c-myc oncogene; anti-microbial agents such as triclosan, cephalosporins, aminoglycosides, nitrofurantoin, silver ions, compounds, or salts; bioflim synthesis inhibitors such as non-steroidal anti-inflammatory agents and chelating agents such as ethylenediaminetetraacetic acid, O,O'-bis(2-aminoethyl)ethyleneglycol-N,N,N',N'-tetraacetic acid and mixtures thereof; antibiotics such as gentamycin, rifampin, minocyclin, and ciprofolxacin; antibodies including chimeric antibodies and antibody fragments; anesthetic agents such as lidocaine, bupivacaine, and ropivacaine; nitric oxide; nitric oxide (NO) donors such as linsidomine, molsidomine, L-arginine, NO-carbohydrate adducts, polymeric or oligomeric NO adducts; anti-coagulants such as D-Phe-Pro-Arg chioromethyl ketone, an RGD peptide-containing compound, heparin, antithrombin compounds, platelet receptor antagonists, anti-thrombin antibodies, anti-platelet receptor antibodies, enoxaparin, hirudin, warfarin sodium, Dicumarol, aspirin, prostaglandin inhibitors, platelet aggregation inhibitors such as cilostazol and tick antiplatelet factors; vascular cell growth promoters such as growth factors, transcriptional activators, and translational promoters; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; agents which interfere with endogenous vascoactive mechanisms; inhibitors of heat shock proteins such as geldanamycin; and any combinations and prodrugs of the above.

Exemplary biomolecules include peptides, polypeptides and proteins; oligonucleotides; nucleic acids such as double or single stranded DNA (including naked and cDNA), RNA, antisense nucleic acids such as antisense DNA and RNA, small interfering RNA (siRNA), and ribozymes; genes; carbohydrates; angiogenic factors including growth factors; cell cycle inhibitors; and anti-restenosis agents. Nucleic acids may be incorporated into delivery systems such as, for example, vectors (including viral vectors), plasmids or liposomes.

Non-limiting examples of proteins include monocyte chemoattractant proteins ("MCP-1) and bone morphogemc proteins ("BMP's"), such as, for example, BMIP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15. Preferred BMPS are any of BMP-2, BMP-3, BMP-4, BMP-5, BMP-6, and BMP-7. These BMPs can be provided as homodimers, heterodimers, or combinations thereof, alone or together with other molecules. Alternatively, or in addition, molecules capable of inducing an upstream or downstream effect of a BMP can be provided. Such molecules include any of the "hedgehog" proteins, or the DNA's encoding them. Non-limiting examples of genes include survival genes that protect against cell death, such as anti-apoptotic Bcl-2 family factors and Akt kinase and combinations thereof. Non-limiting examples of angiogenic factors include acidic and basic fibroblast growth factors, vascular endothelial growth factor, epidermal growth factor, transforming growth factor .alpha. and .beta., platelet-derived endothelial growth factor, platelet-derived growth factor, tumor necrosis factor .alpha., hepatocyte growth factor, and insulin like growth factor. A non-limiting example of a cell cycle inhibitor is a cathespin D (CD) inhibitor. Non-limiting examples of anti-restenosis agents include p15, p16, p18, p19, p21, p27, p53, p57, Rb, nFkB and E2F decoys, thymidine kinase ("TK") and combinations thereof and other agents useful for interfering with cell proliferation.

Exemplary small molecules include hormones, nucleotides, amino acids, sugars, and lipids and compounds have a molecular weight of less than 100 kD.

Exemplary cells include stem cells, progenitor cells, endothelial cells, adult cardiomyocytes, and smooth muscle cells. Cells can be of human origin (autologous or allogenic) or from an animal source (xenogenic), or genetically engineered. Non-limiting examples of cells include side population (SP) cells, lineage negative (Lin⁻) cells including Lin⁻CD34⁻, Lin⁻CD34⁺, Lin⁻cKit⁺, mesenchymal stem cells including mesenchymal stem cells with 5-aza, cord blood cells, cardiac or other tissue derived stem cells, whole bone marrow, bone marrow mononuclear cells, endothelial progenitor cells, skeletal myoblasts or satellite cells, muscle derived cells, go cells, endothelial cells, adult cardiomyocytes, fibroblasts, smooth muscle cells, adult cardiac fibroblasts+5-aza, genetically modified cells, tissue engineered grafts, MyoD scar fibroblasts, pacing cells, embryonic stem cell clones, embryonic stem cells, fetal or neonatal cells, immunologically masked cells, and teratoma derived cells.

Any of the therapeutic agents may be combined to the extent such combination is biologically compatible.

Any of the above mentioned therapeutic agents may be incorporated into a polymeric coating on or in the medical device. The polymers of the polymeric coatings may be biodegradable or non-biodegradable. Non-limiting examples of suitable non-biodegradable polymers include polystyrene; polyisobutylene copolymers and styrene-isobutylene-styrene block copolymers such as styrene-isobutylene-styrene tert-block copolymers (SIBS); polyvinylpyrrolidone including cross-linked polyvinylpyrrolidone; polyvinyl alcohols, copolymers of vinyl monomers such as EVA; polyvinyl ethers; polyvinyl aromatics; polyethylene oxides; polyesters including polyethylene terephthalate; polyamides; polyacrylamides; polyethers including polyether sulfone; polyalkylenes including polypropylene, polyethylene and high molecular weight polyethylene; polyurethanes; polycarbonates, silicones; siloxane polymers; cellulosic polymers such as cellulose acetate; polymer dispersions such as polyurethane dispersions (BAYHYDROL®); ; squalene emulsions; and mixtures and copolymers of any of the foregoing.

Non-limiting examples of suitable biodegradable polymers include polycarboxylic acid, polyanhydrides including maleic anhydride polymers; polyorthoesters; poly-amino acids; polyethylene oxide; polyphosphazenes; polylactic acid, polyglycolic acid and copolymers and mixtures thereof such as poly(L-lactic acid) (PLLA), poly(D,L,-lactide), poly (lactic acid-co-glycolic acid), 50/50 (DL-lactide-co-glycolide); polydioxanone; polypropylene fumarate; polydepsipeptides; polycaprolactone and co-polymers and mixtures thereof such as poly(D,L-lactide-co-caprolactone) and poly-caprolactone co-butylacrylate; polyhydroxybutyrate valerate and blends; polycarbonates such as tyrosine-derived polycarbonates and arylates, polyiminocarbonates, and polydimethyltrimethylcarbonates; cyanoacrylate; calcium phosphates; polyglycosaminoglycans; macromolecules such as polysaccharides (including hyaluronic acid; cellulose, and hydroxypropylmethyl cellulose; gelatin; starches; dextrans; alginates and derivatives thereof), proteins and polypeptides; and mixtures and copolymers of any of the foregoing. The biodegradable polymer may also be a surface erodable polymer such as polyhydroxybutyrate and its copolymers, polycaprolactone, polyanhydrides (both crystalline and amorphous), maleic anhydride copolymers, and zinc-calcium phosphate.

Such materials used with the present invention may be formed by any method known to one in the art. For example, an initial polymer/solvent mixture can be formed and then the therapeutic agent added to the polymer/solvent mixture. Alternatively, the polymer, solvent, and therapeutic agent can be added simultaneously to form the mixture. The polymer/solvent mixture may be a dispersion, suspension or a solution. The therapeutic agent may also be mixed with the polymer in the absence of a solvent. The therapeutic agent may be dissolved in the polymer/solvent mixture or in the polymer to be in a true solution with the mixture or polymer, dispersed into fine or micronized particles in the mixture or polymer, suspended in the mixture or polymer based on its solubility profile, or combined with micelle-forming compounds such as surfactants or adsorbed onto small carrier particles to create a suspension in the mixture or polymer. The material may comprise multiple polymers and/or multiple therapeutic agents.

A coating can be applied to the medical device by any known method in the art including dipping, spraying, rolling, brushing, electrostatic plating or spinning, vapor deposition, air spraying including atomized spray coating, and spray coating using an ultrasonic nozzle.

The coating is typically from about 1 to about 50 microns thick Very thin polymer coatings, such as about 0.2-0.3 microns and much thicker coatings, such as more than 10 microns, are also possible. It is also within the scope of the present invention to apply multiple layers of polymer coatings onto the medical device. Such multiple layers may contain the same or different therapeutic agents and/or the same or different polymers. Methods of choosing the type, thickness and other properties of the polymer and/or therapeutic agent to create different release kinetics are well known to one in the art.

The medical device may also contain a radio-opacifying agent within its structure to facilitate viewing the medical device during insertion and at any point while the device is implanted. Non-limiting examples of radio-opacifying agents are bismuth subcarbonate, bismuth oxychloride, bismuth trioxide, barium sulfate, tungsten, and mixtures thereof.

It is contemplated that a device of the present invention may also embody any combination of the previously mentioned features and embodiments. Accordingly, the scope of the invention is not limited to the exact embodiments described herein.

What is claimed is:

1. A therapeutic delivery device for delivery of therapeutic to a target site within the body of a patient comprising:
   a first catheter having an internal lumen;
   an expandable multi-port housing forming a first chamber fluidly coupled to an end of the first catheter,
      the multi-port housing sized to travel within a lumen of the patient,
      the multi-port housing adapted to expand from a first configuration to a second configuration, the second configuration being larger than the first configuration,
      the multi-port housing containing at least two ejection ports, at least one of the ejection ports fluidly coupled to an internal lumen of the multi-port housing;
   a shunt forming a second chamber within the multi-port housing, the shunt configured to allow fluid to flow through an outer wall of the multi-port housing when the multi-port housing is deployed in the body of a patient, the second chamber being isolated from the first chamber to prevent fluid communication between the first and second chambers; and
   a second catheter, the second catheter slidable within the first catheter.

2. The therapeutic delivery device of claim 1 wherein the multi-port housing is an expandable bladder and wherein at least one of the ejection ports is raised above an external surface of the expandable bladder.

3. The therapeutic delivery device of claim 2 wherein the ejection ports are positioned on top of truncated cones extending from the expandable bladder.

4. The therapeutic delivery device of claim 2 wherein the expandable bladder is sized to conform to a vessel within the heart of a patient when the expandable bladder is in an expanded configuration.

5. The therapeutic delivery device of claim 2 wherein the ejection ports have piercing tips.

6. The therapeutic delivery device of claim 2 wherein the ejection ports are metallic.

7. The therapeutic delivery device of claim 2 wherein the expandable bladder includes a first bypass valve and a second bypass valve.

8. The therapeutic delivery device of claim 2 wherein the expandable bladder includes a partition dividing the housing into at least the first chamber and the shunt forming the second chamber.

9. A therapeutic delivery device for delivery of therapeutic to a target site within the body of a patient comprising:
   a first catheter having an internal lumen;
   an expandable multi-port housing fluidly coupled to an end of the first catheter,
      the multi-port housing adapted to expand from a first configuration to a second configuration, the second configuration being larger than the first configuration,
      the multi-port housing comprises at least two arms extending from an apex point coupled to the first catheter and each of the arms defining an internal lumen,
      each of the arms comprising a free distal end with an ejection port at the free distal end, the free distal end configured to penetrate into the target tissue, the ejection port of each arm fluidly coupled to the internal lumen of its respective arm;
   a housing wrap coupled to and encircling a portion of the arms, the free distal ends of the arms extending past a distal edge of the wrap to limit the distance the ports penetrate into the target site during delivery of the therapeutic; and
   a sheath initially positioned around the multi-port housing, the arms, and the housing wrap, the multi-port housing slidable into the sheath and out of the sheath such that when the delivery device is positioned within the body of a patient the arms expand when outside of the sheath and contract when inside of the sheath.

10. The therapeutic delivery system of claim 9 wherein at least one of the ejection ports has a piercing tip.

11. The therapeutic delivery system of claim 9 wherein the arms fan out from the apex point.

12. The therapeutic delivery system of claim 9 wherein the arms are fluidly connected to the first catheter through the apex.

* * * * *

UNITED STATES PATENT AND TRADEMARK OFFICE
CERTIFICATE OF CORRECTION

PATENT NO. : 7,470,252 B2
APPLICATION NO. : 10/942046
DATED : December 30, 2008
INVENTOR(S) : Mickley et al.

It is certified that error appears in the above-identified patent and that said Letters Patent is hereby corrected as shown below:

Abstract, line 1, "provides a systems that delivers" should be changed to --provides systems that deliver--;
Column 3, line 5, "delivery" should be changed to --deliver--;
Column 4, line 19, "second chamber 421" should be changed to
--second chamber 420--;
Column 6, line 14, "virus" should be changed to --viruses--;
Column 6, line 15, "a-virus" should be changed to --α-virus--;
Column 6, line 52, "chioromethylketone" should be changed to --chloromethylketone--;
Column 7, line 15, "("MCP-1)" should be changed to --("MCP-1")--;
Column 7, line 16, "("BMP's")" should be changed to --("BMPs")--;
Column 7, line 19, "BMPS" should be changed to --BMPs--;
Column 7, line 25, "DNA's" should be changed to --DNAs--;
Column 7, line 31-32, "transforming growth factor .alpha. and .beta." should be changed to --transforming growth factor α and β--;
Column 7, line 33, "tumor necrosis factor .alpha." should be changed to --tumor necrosis factor α--;
Column 7, line 42, "have" should be changed to --having--;
Column 7, line 55, "go cells" should be changed to --$G_0$--;
Column 8, line 20, "poly(D,L,-lactide)" should be changed to --poly(D,L-lactide)--;
Column 8, line 21, "50/50 (DL-lactide-co-glycolide)" should be changed to --50/50 (D,L-lactide-co-glycolide)--;
and
Column 8, line 62, "thick" should be changed to --thick.--.

Signed and Sealed this

Twenty-ninth Day of September, 2009

David J. Kappos
*Director of the United States Patent and Trademark Office*